United States Patent
Koizumi et al.

(10) Patent No.: US 10,288,598 B2
(45) Date of Patent: May 14, 2019

(54) ELECTROSTATIC CAPACITANCE DETECTION DEVICE

(71) Applicant: Aisin Seiki Kabushiki Kaisha, Kariya-shi (JP)

(72) Inventors: Takaaki Koizumi, Obu (JP); Takehiro Tabata, Kariya (JP)

(73) Assignee: AISIN SEIKI KABUSHIKI KAISHA, Kariya-shi (JP)

( * ) Notice: Subject to any disclaimer, the term of this patent is extended or adjusted under 35 U.S.C. 154(b) by 246 days.

(21) Appl. No.: 15/290,347

(22) Filed: Oct. 11, 2016

(65) Prior Publication Data

US 2017/0122927 A1 May 4, 2017

(30) Foreign Application Priority Data

Oct. 30, 2015 (JP) ................................ 2015-214785

(51) Int. Cl.
| | |
|---|---|
| *G01N 33/483* | (2006.01) |
| *G01N 27/22* | (2006.01) |
| *H03K 17/96* | (2006.01) |
| *H03K 17/955* | (2006.01) |

(52) U.S. Cl.
CPC ....... *G01N 33/4833* (2013.01); *G01N 27/221* (2013.01); *H03K 17/955* (2013.01); *H03K 17/962* (2013.01)

(58) Field of Classification Search
USPC ................................................ 324/658–690
See application file for complete search history.

(56) References Cited

U.S. PATENT DOCUMENTS

| 8,217,666 | B2 | 7/2012 | Hagimoto et al. | |
|---|---|---|---|---|
| 2007/0089527 | A1 | 4/2007 | Shank et al. | |
| 2009/0073140 | A1* | 3/2009 | Fujita | H03K 17/962 345/174 |
| 2009/0262548 | A1* | 10/2009 | Ando | B60Q 3/82 362/544 |

(Continued)

FOREIGN PATENT DOCUMENTS

| DE | 10 2011 010 620 A1 | 8/2012 |
|---|---|---|
| FR | 2 968 485 A1 | 6/2012 |

(Continued)

OTHER PUBLICATIONS

Extended European Search Report dated Mar. 30, 2017 in Patent Application No. 16194700.7.

(Continued)

*Primary Examiner* — Vincent Q Nguyen
(74) *Attorney, Agent, or Firm* — Oblon, McClelland, Maier & Neustadt, L.L.P.

(57) ABSTRACT

An electrostatic capacitance detection device includes: an electrostatic capacitance sensor; and a control device that controls the electrostatic capacitance sensor, wherein the control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount.

8 Claims, 10 Drawing Sheets

(56) References Cited

U.S. PATENT DOCUMENTS

| | | | | |
|---|---|---|---|---|
| 2010/0044121 A1* | 2/2010 | Simon | ................ | G06F 3/03547 |
| | | | | 178/18.03 |
| 2010/0219840 A1 | 9/2010 | Motojima et al. | | |
| 2016/0313843 A1* | 10/2016 | Vanga | ................ | G06F 3/0416 |

FOREIGN PATENT DOCUMENTS

| | | |
|---|---|---|
| JP | 2007-018811 A | 1/2007 |
| JP | 2007-027034 A | 2/2007 |
| JP | 2009-229248 A | 10/2009 |
| JP | 2011-17642 | 1/2011 |
| JP | 2012-129762 | 7/2012 |
| JP | 2012-138026 A | 7/2012 |
| WO | 2012/137876 A1 | 10/2012 |

OTHER PUBLICATIONS

Japanese Office Action issued in Japanese Patent Application No. 2015-214785 dated Apr. 2, 2019, citing documents AO-AS therein (w/ English translation).

* cited by examiner

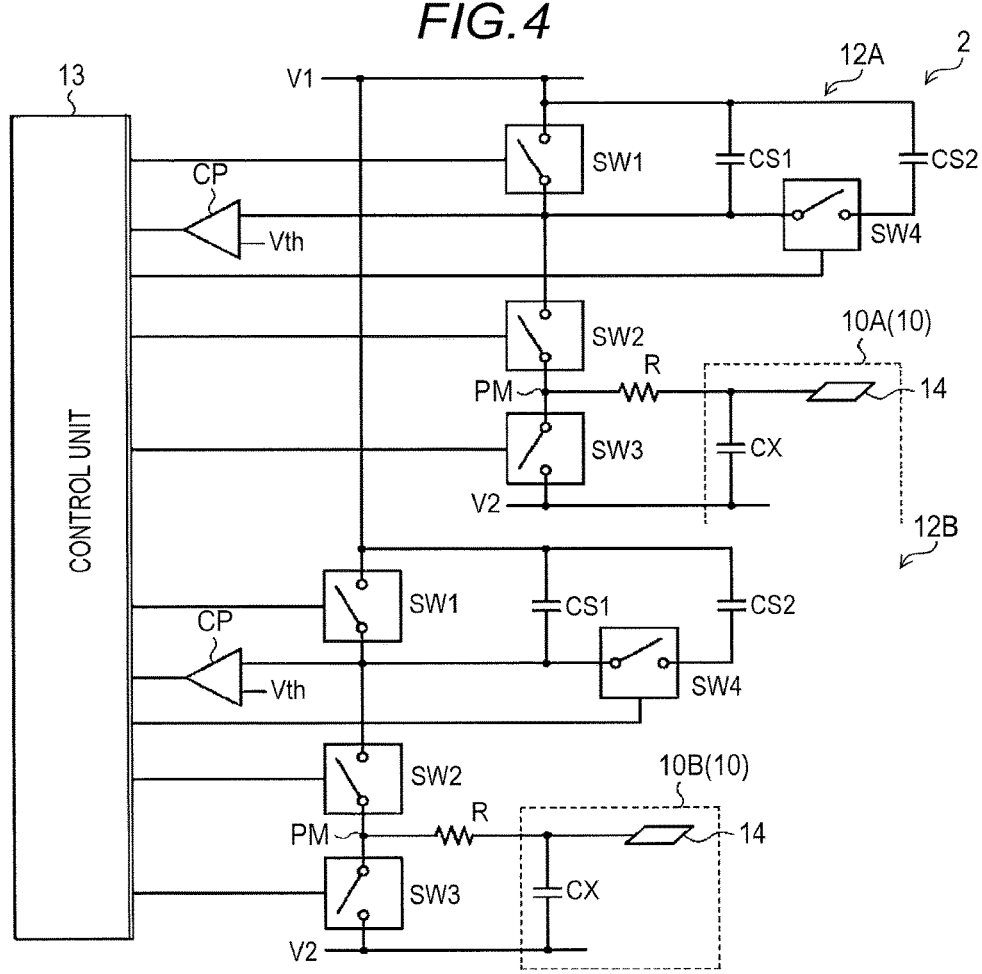

FIG.4

FIG.5A
(HIGH-RESOLUTION DETECTION MODE)

| NUMBER-OF-SWITCHINGS DIFFERENCE $\triangle Na$ | DETERMINATION |
|---|---|
| $\triangle Na < NUM1$ | NON-DETECTION(N) |
| $NUM1 \leq \triangle Na < NUM2$ | APPROACH DETECTION(A) |
| $NUM3 \leq \triangle Na$ | CONTACT DETECTION(C) |

FIG.5B
(LOW-RESOLUTION DETECTION MODE)

| NUMBER-OF-SWITCHINGS DIFFERENCE $\triangle Nb$ | DETERMINATION |
|---|---|
| $\triangle Nb < NUM4$ | NON-DETECTION(N) |
| $NUM4 \leq \triangle Nb$ | CONTACT DETECTION(C) |

FIG.10
| TIME | PATTERN 1 | PATTERN 2 |
|---|---|---|
| FIRST PERIOD T1 | NON-DETECTION(N) | NON-DETECTION(N) |
| SECOND PERIOD T2 | NON-DETECTION(N) | CONTACT DETECTION(C) |
| THIRD PERIOD T3 | APPROACH DETECTION(A) | CONTACT DETECTION(C) |
| FOURTH PERIOD T4 | CONTACT DETECTION(C) | CONTACT DETECTION(C) |
| OVERALL DETERMINATION RESULT | PERSON OR HAND | WATER |
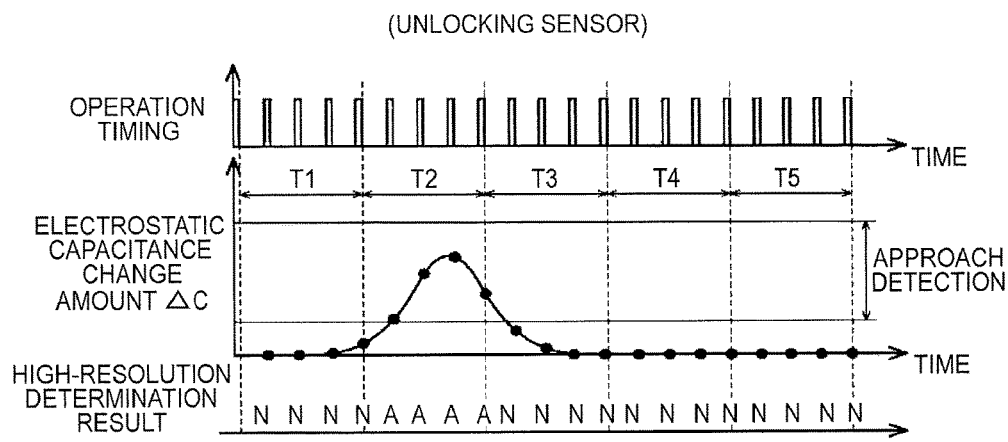
FIG.11A
(UNLOCKING SENSOR)
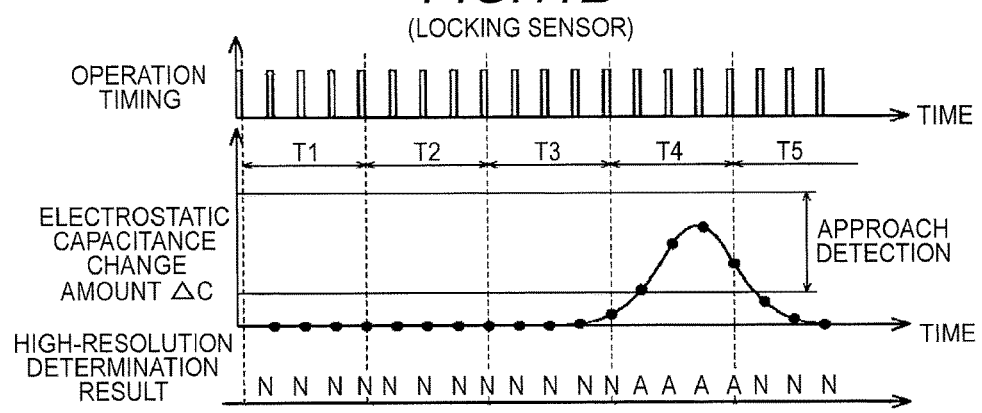
FIG.11B
(LOCKING SENSOR)

FIG.12

| TIME | UNLOCKING SENSOR PATTERN | LOCKING SENSOR PATTERN |
|---|---|---|
| FIRST PERIOD T1 | NON-DETECTION(N) | NON-DETECTION(N) |
| SECOND PERIOD T2 | APPROACH DETECTION(A) | NON-DETECTION(N) |
| THIRD PERIOD T3 | NON-DETECTION(N) | NON-DETECTION(N) |
| FOURTH PERIOD T4 | NON-DETECTION(N) | APPROACH DETECTION(A) |
| FIFTH PERIOD T5 | NON-DETECTION(N) | NON-DETECTION(N) |
| OVERALL DETERMINATION RESULT | SLIDE GESTURE | |

ELECTROSTATIC CAPACITANCE DETECTION DEVICE

CROSS REFERENCE TO RELATED APPLICATIONS

This application is based on and claims priority under 35 U.S.C. § 119 to Japanese Patent Application 2015-214785, filed on Oct. 30, 2015, the entire contents of which are incorporated herein by reference.

TECHNICAL FIELD

This disclosure relates to an electrostatic capacitance detection device that detects an object.

BACKGROUND DISCUSSION

Electrostatic capacitance detection devices that detect contact or approach of objects are known. An electrostatic capacitance detection device includes an electrostatic capacitance sensor and determines presence or absence of contact or approach of an object based on a change in electrostatic capacitance of the electrostatic capacitance sensor at the time of contact or approach of the object to the electrostatic capacitance sensor. For example, an electrostatic capacitance detection device is contained in a door handle of a vehicle. The electrostatic capacitance detection device detects contact or approach of a hand of a person to the door handle (for example, see JP 2011-17642A (Reference 1)).

Electrostatic capacitance detection devices of the related art each detect a change amount of electrostatic capacitance of an electrostatic capacitance sensor and determine presence or absence of contact or approach of a hand of a person based on whether the change amount is greater than a set value. Incidentally, modes of contact or approach of an object are diverse and a problem occurs in that modes which can be detected in electrostatic capacitance detection devices of the related art are restricted.

SUMMARY

Thus, a need exists for an electrostatic capacitance detection device which is not suspectable to the drawback mentioned above.

(1) An electrostatic capacitance detection device according to an aspect of this disclosure includes an electrostatic capacitance sensor and a control device that controls the electrostatic capacitance sensor. The control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount. The electrostatic capacitance detection device with the foregoing configuration can detect the plurality of change modes in which phases are different in a change in the electrostatic capacitance.

BRIEF DESCRIPTION OF THE DRAWINGS

The foregoing and additional features and characteristics of this disclosure will become more apparent from the following detailed description considered with the reference to the accompanying drawings, wherein:

FIG. 4 is a circuit diagram illustrating an electrostatic capacitance detection device according to an embodiment;

FIG. 5A is a table illustrating a relation between a difference in the number of switchings and determination content in a high-resolution detection mode and FIG. 5B is a table illustrating a relation between a difference in the number of switchings and determination content in a low-resolution detection mode;

FIG. 10 is a table illustrating a relation between a determination result pattern and an overall determination result;

FIG. 11A is a diagram illustrating a relation among an operation timing of the high-resolution detection mode, a transition of the electrostatic capacitance change amount of the electrostatic capacitance sensor, and a determination result in an unlocking sensor and FIG. 11B is a diagram illustrating a relation among an operation timing of the high-resolution detection mode, a transition of the electrostatic capacitance change amount of the electrostatic capacitance sensor, and a determination result in a locking sensor;

FIG. 12 is a table illustrating a relation between a determination result pattern and an overall determination result;

DETAILED DESCRIPTION

An electrostatic capacitance detection device will be described with reference to FIGS. 1 to 16.

Figure 1:
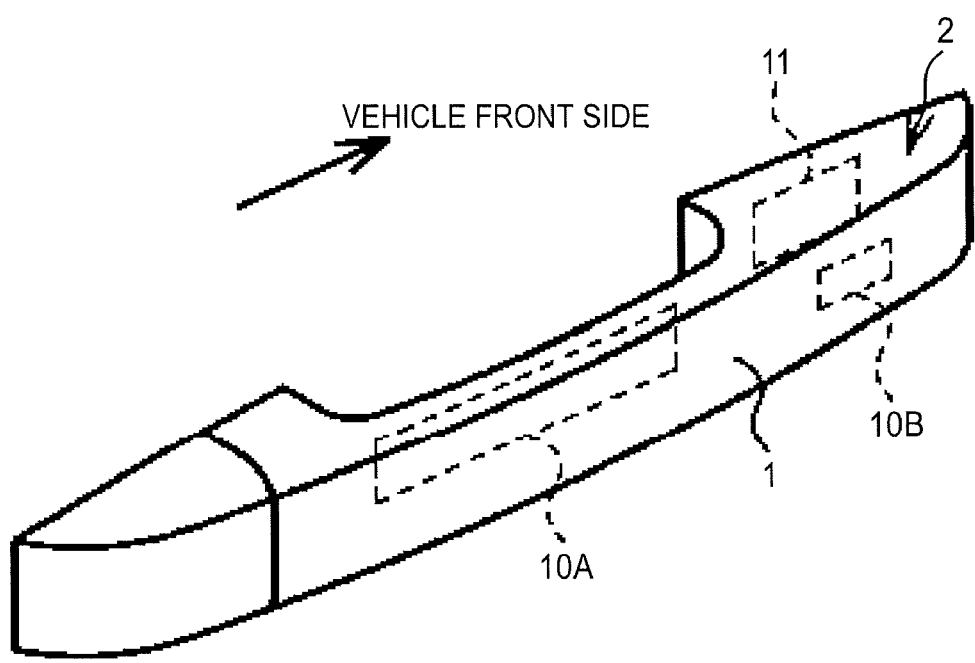
FIG. 1 is a perspective view illustrating a door handle.

As illustrated in FIG. 1, an electrostatic capacitance detection device 2 is equipped in, for example, a door handle 1 of a vehicle door. The electrostatic capacitance detection device 2 detects a hand of a person coming into contact with the door handle 1 or water applied to the door handle 1. Hereinafter, the electrostatic capacitance detection device 2 contained in the door handle 1 will be described.

Basic Configuration

Figure 2:
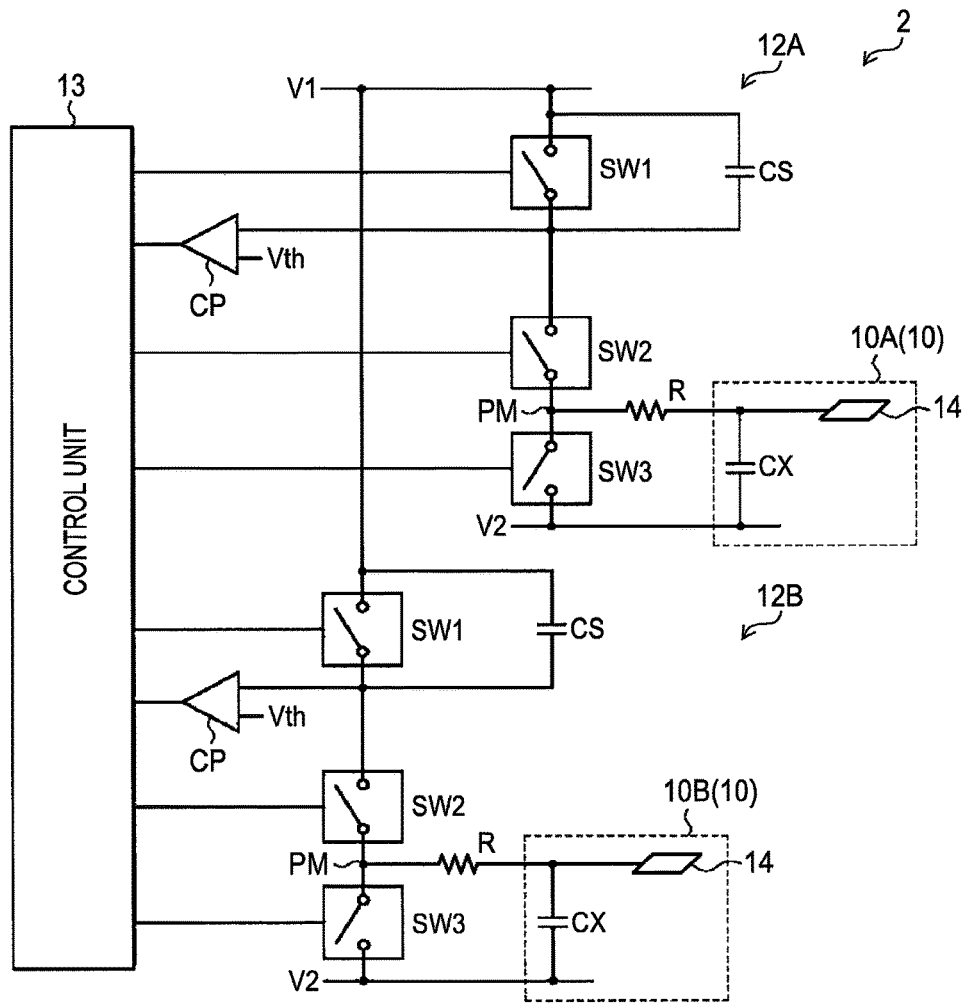
FIG. 2 is a circuit diagram illustrating a basic configuration of an electrostatic capacitance detection device.

A basic configuration of the electrostatic capacitance detection device 2 will be described with reference to FIG. 2. The electrostatic capacitance detection device 2 includes two electrostatic capacitance sensors and a control device 11 (see FIG. 1). One of the two electrostatic capacitance sensors is an unlocking sensor (hereinafter referred to as an "unlocking sensor 10A) of the vehicle door and the other electrostatic capacitance sensor is a locking sensor (hereinafter referred to as a "locking sensor 10B") of the vehicle door. The unlocking sensor 10A and the locking sensor 10B are separated by a preset distance (set distance).

When the unlocking sensor 10A and the locking sensor 10B are not distinguished from each other in description, the unlocking sensor 10A and the locking sensor 10B are simply referred to as electrostatic capacitance sensors 10. The unlocking sensor 10A is disposed in a middle portion and on the inside (a portion facing to the outer surface of the vehicle door) of the door handle 1. The locking sensor 10B is disposed on the front side and on the outside of the door handle 1.

The electrostatic capacitance sensor 10 includes an electrode 14 that has a flat surface or a curved surface. Preferably, a conductive member that has the same structure as the electrode 14 and has a flat surface or a curved surface is disposed to face the electrode 14 and to be separate by a predetermined distance. The electrostatic capacitance sensor 10 has predetermined capacitance. The electrostatic capacitance of the electrostatic capacitance sensor 10 increases due to direct or indirect contact of an object or disposition of an object near the electrostatic capacitance sensor 10. That is, the electrostatic capacitance sensor 10 includes a capacitor (hereinafter referred to as a "sensor capacitor CX") of which electrostatic capacitance is changed due to an external factor (contact or approach of an object).

The control device 11 detects an amount corresponding to a change amount of the electrostatic capacitance (hereinafter referred to as a "capacitance change amount") of the electrostatic capacitance sensor 10.

The control device 11 includes a first circuit unit 12A connected to the unlocking sensor 10A, a second circuit unit 12B connected to the locking sensor 10B, and a control unit 13 controlling the first circuit unit 12A and the second circuit unit 12B. The basic configuration of the first circuit unit 12A is the same as the basic configuration of the second circuit unit 12B. On the other hand, the magnitudes of set potentials Vth have different values between the first circuit unit 12A and the second circuit unit 12B with respect to the magnitude of the electrostatic capacitance of a standard capacitor CS and the magnitudes of the electrodes 14 and the like.

The first circuit unit 12A includes the standard capacitor CS, three switches (hereinafter referred to as a "first switch SW1" to a "third switch SW3") of which operations are controlled by the control unit 13, and a potential determination device CP.

The standard capacitor CS is connected to the electrostatic capacitance sensors 10 in series. Specifically, the standard capacitor CS and the electrostatic capacitance sensors 10 are disposed in series between a first potential source and a second potential source. The first potential source has higher potential than the second potential source. The second potential source can be grounded. One end of the standard capacitor CS is connected to the first potential source and the other end thereof is connected to the second potential source. The electrodes 14 of the electrostatic capacitance sensors 10 are connected between the standard capacitor CS and the second potential source. The electrode 14 is capacitance-coupled with the second potential source with a space therebetween. The electrostatic capacitance of the electrostatic capacitance sensor 10 is changed due to presence or absence of contact or approach of an object to the electrode 14. Examples of the object conceptually include a hand of a person, an object such as a cloth or a bag, and a fluid such as water.

The first switch SW1 is connected to the standard capacitor CS in parallel. The second switch SW2 is connected between the standard capacitor CS and the electrode 14 of the electrostatic capacitance sensor 10. One end of the second switch SW2 is connected to the standard capacitor CS and the other end thereof is connected to the electrode 14 via a resistor R. The other end of the second switch SW2 is connected to the second potential source via the third switch SW3. The third switch SW3 is connected to the electrostatic capacitance sensor 10 in parallel. One end of the third switch SW3 is connected to the side of the electrode 14 via the resistor R and the other end thereof is connected to the second potential source.

The potential determination device CP compares the set potential Vth to a potential (hereinafter referred to as a middle potential VM) of a position (hereinafter referred to as a "middle position PM") between the standard capacitor CS and the electrostatic capacitance sensor 10 (that is, between the standard capacitor CS and the electrode 14) to determine whether the middle potential VM is less than the set potential Vth. The potential determination device CP outputs an initial signal when the middle potential VM is equal to or greater than the set potential Vth, and outputs an end signal when the middle potential VM is less than the set potential Vth. The potential determination device CP can be configured to include a comparator.

Figure 3:
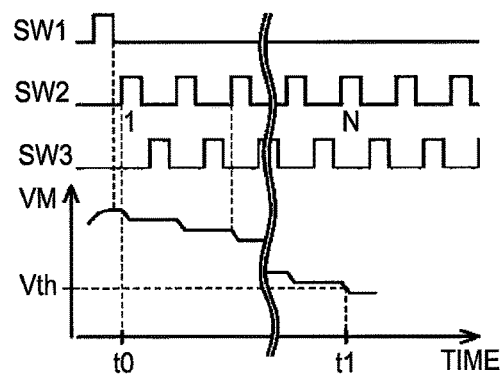
FIG. 3 is a diagram illustrating a relation between operation timings of first, second, and third switches and a voltage displacement graph indicating a change in a potential at a middle position.

Switching control performed to detect a capacitance change amount (that is, an amount corresponding to a change amount of electrostatic capacitance of the electrostatic capacitance sensor 10) of the electrostatic capacitance sensor 10 will be described with reference to FIG. 3.

The first switch SW1, the second switch SW2, and the third switch SW3 operate at a predetermined period. In an initial stage of the period, the first switch SW1 is controlled to a closed state and the second switch SW2 and the third switch SW3 are controlled to an open state. Thus, the standard capacitor CS is initialized so that the potential of the middle position PM becomes identical to a potential V1 of the first potential source. In the following description, a potential of the middle position PM at the time of the initialization of the standard capacitor CS is referred to as an "initial potential" (which is the same as the potential V1).

Next, the first switch SW1 is controlled to the open state, the second switch SW2 is controlled to the closed state, and the third switch SW3 maintains the open state (hereinafter, this switch operation is referred to as a "second switch closing operation"). At this time, a current flows to the standard capacitor CS and the sensor capacitor CX, so that the middle potential VM is lowered.

Next, the first switch SW1 is maintained in the open state, the second switch SW2 is controlled to the open state, and the third switch SW3 is controlled to the closed state (hereinafter, this switch operation is referred to as a "third switch closing operation").

While the first switch SW1 maintains the open state, the second switch closing operation and the third switch closing operation are alternately repeated. Therefore, as illustrated in FIG. 3, the middle potential VM is gradually lowered. When the middle potential VM is less than the set potential Vth, the potential determination device CP outputs the end signal to the control unit 13.

The control unit 13 counts the number of second switch closing operations performed from the beginning of the period to reception of the end signal at each period (that is, the number of connections: hereinafter referred to as the "number of switchings"). That is, the control unit 13 counts a period (a period from time t0 to time t1) in which the middle potential VM reaches the set potential Vth from the initial potential (the number of second switch closing operations (the number of connections)).

Further, the control unit 13 stores the number of switchings N for each period in chronological order or in association with a chronological parameter. Then, the control unit 13 calculates a difference in the number of switchings N (hereinafter referred to as a number-of-switchings difference ΔN) between two time points. The number-of-switchings difference ΔN is defined as a difference between the number of switchings N1 (the number of first connections) obtained at a time point before calculation of the number-of-switchings difference ΔN and the number of switchings N2 (the number of second connections) obtained at this calculation time point. That is, "number-of-switchings difference ΔN"="-(the number of switchings N2 at calculation time point–the number of switchings N1 at time point before calculation". The time point before the calculation indicates a time point earlier by a predetermined period than the calculation time point or a time point before a predetermined time.

Next, the control unit 13 determines whether the number-of-switchings difference ΔN to a set value NUM to determine whether the number-of-switchings difference ΔN is greater than the set value NUM. The set value NUM indicates a lower limit of a range in which the number-of-switchings difference ΔN can be taken in a case of contact or approach of an object to the electrostatic capacitance sensor 10. The control unit 13 determines that the object is in contact or has approached the electrostatic capacitance sensor 10 when the number-of-switchings difference ΔN is greater than the set value NUM. Hereinafter, the determination of presence or absence of the contact or approach of the object to the electrostatic capacitance sensor 10 performed through the comparison between the number-of-switchings difference ΔN and the set value NUM by the control unit 13 is referred to as "detection determination".

Here, a technical meaning of the number-of-switchings difference ΔN will be described.

As described above, the standard capacitor CS is initialized through the first switch closing operation and the middle potential VM becomes the initial potential. Subsequently, the middle potential VM is gradually lowered through alternate repetition of the second switch closing operation and the third switch closing operation. A speed at which the middle potential VM is lowered is changed according to the magnitude of the electrostatic capacity of the electrostatic capacitance sensor 10. Specifically, as the electrostatic capacity of the electrostatic capacitance sensor 10 is larger, the middle potential VM is lowered faster. The slowness of lowering of the middle potential VM (that is, the length of a time in which the middle potential VM reaches the set potential Vth from the initial potential) is correlated to the number of switches N. Accordingly, a change amount of the electrostatic capacitance of the electrostatic capacitance sensor 10 can be associated with the number-of-switchings difference ΔN between two time points. In terms of this fact, the number-of-switchings difference ΔN between two time points is used as a parameter for determining whether an object comes into contact with or is approaching the electrostatic capacitance sensor 10.

Specifically, when the electrostatic capacitance of the electrostatic capacitance sensor 10 increases due to contact or approach of an object to the electrostatic capacitance sensor 10, the number of switchings N obtained through switching control decreases and the number-of-switchings difference ΔN (the number of decreases) increases. That is, the increase in the number-of-switchings difference ΔN means the contact or approach of the object to the electrostatic capacitance sensor 10.

When the number-of-switchings difference ΔN corresponding to a capacitance change amount of the electrostatic capacitance of the electrostatic capacitance sensor 10 is obtained, the numbers of switchings N1 and N2 between two time points are used due to the following reason. The electrostatic capacitance of the electrostatic capacitance sensor 10 is changed by a factor other than contact or approach of an object, for example, an environment (for example, temperature). That is, the electrostatic capacitance of the electrostatic capacitance sensor 10 can be changed even in a case in which there is no contact or approach of an object. Therefore, when the number of switchings N1 serving as a standard at the time of calculation of the number-of-switchings difference ΔN is set to a fixed value, the number-of-switchings difference ΔN obtained in this way may include a change based on a factor other than contact or approach of an object, and thus may be inappropriate as a parameter for accurately determining the contact or approach of the object. In contrast, when the number of switchings N1 serving as a standard is set to a value obtainable at a time point earlier by a predetermined time than a calculation time point at which the number-of-switchings difference ΔN between two time points is calculated, environments at both time points can be regarded to be substantially the same. Therefore, the number-of-switchings difference ΔN does not include a change based on a factor other than contact or approach of an object. Accordingly, using the number-of-switchings difference ΔN between two time points, it is possible to accurately determine contact or approach of an object. Because of this reason, in an embodiment, the number-of-switchings difference ΔN between two time points is used as a parameter for accurately determining contact or approach of an object.

First Embodiment

An electrostatic capacitance detection device 2 according to a first embodiment disclosed herein will be described with reference to FIG. 4.

The electrostatic capacitance detection device 2 according to the present embodiment is different from the electrostatic capacitance detection device 2 with the basic configuration in the following points.

In the basic configuration of the electrostatic capacitance detection device 2, the standard capacitor CS is configured by one capacitor. In the present embodiment, a standard capacitor CS is configured by a plurality of sub-capacitors. In the example illustrated in FIG. 4, the standard capacitor CS is configured to include two sub-capacitors (hereinafter referred to as a "first sub-capacitor CS1" and a "second sub-capacitor CS2"). The two sub-capacitors CS1 and CS2 are connected in parallel.

The electrostatic capacitance detection device 2 includes a fourth switch SW4 which switches the electrostatic capacitance of the standard capacitor CS. In the present embodiment, the fourth switch SW4 is installed in one of the two sub-capacitors CS1 and CS2. That is, one sub-capacitor between the two sub-capacitors CS1 and CS2 is installed to be connected in parallel or to be unconnected to the other switch based on an operation of the fourth switch SW4.

The control unit 13 changes the standard capacitor CS through the operation of the fourth switch SW4. That is, the control unit 13 sets the electrostatic capacitance of the standard capacitor CS to the electrostatic capacitance of the first sub-capacitor CS1 by controlling the fourth switch SW4 to the open state and sets the electrostatic capacitance of the standard capacitor CS to the sum of the electrostatic capacitance of the first sub-capacitor CS1 and the second sub-capacitor CS2 by controlling the fourth switch SW4 to the closed state.

In a case in which the standard capacitor CS has a large capacity, a time in which the potential of the middle position PM reaches the set potential Vth from the initial potential is long. Therefore, there are the characteristics that a period at which the control unit 13 obtains the number of switchings N is long. On the other hand, because of the characteristics that the time in which the potential of the middle position PM reaches the set potential Vth from the initial potential is long, even when a change amount of the electrostatic capacitance of the electrostatic capacitance sensor 10 is small, the change amount can be detected as the number-of-switchings difference ΔNa. That is, when the standard capacitor CS has a large capacity, a change in the electrostatic capacitance of the electrostatic capacitance sensor 10 is detected at high resolution.

When the standard capacitor CS has a small capacity, a time in which the potential of the middle position PM reaches the set potential Vth from the initial potential is short. Therefore, there are the characteristics that a period at which the control unit 13 obtains the number of switchings N is short. On the other hand, because of the characteristics that the time in which the potential of the middle position PM reaches the set potential Vth from the initial potential is short, even when a change amount of the electrostatic capacitance of the electrostatic capacitance sensor 10 is small, it is difficult to detect the change amount as the number-of-switchings difference ΔNb. That is, when the standard capacitor CS has a small capacity, a change in the electrostatic capacitance of the electrostatic capacitance sensor 10 is detected at low resolution.

The control unit 13 has two detection modes utilizing the characteristics in the case in which the standard capacitor CS has the high capacity and the characteristics in the case in which the standard capacitor CS has the low capacity. That is, the control unit 13 has a high-resolution detection mode and a low-resolution detection mode. The resolution is defined in such a manner that the number of switchings N increases when the electrostatic capacitance of the electrostatic capacitance sensor 10 increases by a regulated amount.

In the high-resolution detection mode, the control unit 13 detects a capacitance change amount of the electrostatic capacitance sensor 10 at high resolution by controlling the fourth switch SW4 to the closed state and operating the standard capacitor CS as a capacitor having high electrostatic capacitance. Thus, the control unit 13 detects a state in which an object is approaching the electrostatic capacitance sensor 10 and in which the object is not in contact with the electrostatic capacitance sensor 10 (hereinafter referred to as an "approach state") with high precision. Hereinafter, detection of the approach state is referred to as "approach detection".

As illustrated in FIG. 5A, in the high-resolution detection mode, the control unit 13 determines that an object is in a state in which the object is not in contact with the electrostatic capacitance sensor 10 (hereinafter referred to as a "non-detection state") when a number-of-switchings difference ΔNa serving as a capacitance change amount is less than a first set value NUM1. Hereinafter, this determination result is referred to as "non-detection (N)".

The control unit 13 determines that an object is in an approach state in which the object approaches the electrostatic capacitance sensor 10 when the number-of-switchings difference ΔNa is equal to or greater than the first set value NUM1 and is less than a second set value NUM2. This determination result is referred to as "approach detection (A)". The "approach state in which an object approaches" includes a state in which an object is approaching (a state in which an object approaching operation is continued) and a state in which an object has approached (a state in which an approaching operation is completed or a state in which an object is separated from the electrostatic capacitance sensor and is stopped or is near the electrostatic capacitance sensor without being stopped).

When the number-of-switchings difference ΔNa is equal to or greater than a third set value NUM3, the control unit 13 determines that an object is in a contact state in which the object is in contact with the electrostatic capacitance sensor 10. Hereinafter, this determination result is referred to as "contact detection (C)".

The first set value NUM1, the second set value NUM2, and the third set value NUM3 have a relation of the first set value NUM1<the second set value NUM2<the third set value NUM3. The reason why the second set value NUM2 and the third set value NUM3 are not the same value, that is, the reason why an upper limit of the approach detection and a lower limit of the contact detection are not the same value, is to suppress erroneous detection in which an object is detected as the approach detection irrespective of the fact that the object is in contact.

In the low-resolution detection mode, the control unit 13 detects a capacitance change amount of the electrostatic capacitance sensor 10 at low resolution by controlling the fourth switch SW4 to the open state and operating the standard capacitor CS as a capacitor having low electrostatic capacitance.

As illustrated in FIG. 5B, in the low-resolution detection mode, the control unit 13 determines that an object is not in contact with the electrostatic capacitance sensor 10 when a number-of-switchings difference ΔNb serving as a capacitance change amount is less than a set value NUM4 ("non-detection (N)" determination). The control unit 13 determines that an object is in contact with the electrostatic capacitance sensor 10 when the number-of-switchings difference ΔNb serving as the capacitance change amount is equal to or greater than the fourth set value NUM4 ("contact detection C" determination). In this example, since the resolution is low, determination of a state in which an object approaches the electrostatic capacitance sensor 10 (that is, the approach state) is not performed.

The control unit 13 performs switching control of the low-resolution detection mode and switching control of the high-resolution detection mode according to predetermined rules.

For example, the control unit 13 alternately performs the switching control of the low-resolution detection mode and the switching control of the high-resolution detection mode.

Figure 6A:
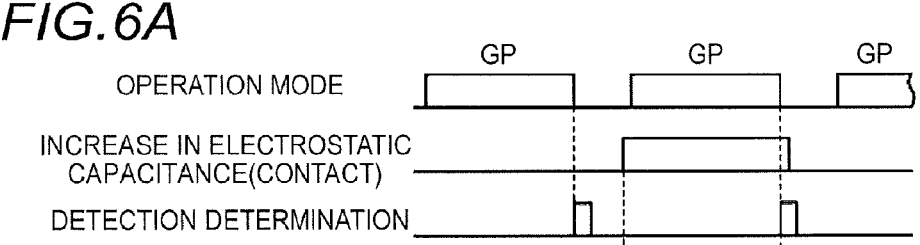
FIG. 6A is a diagram illustrating a relation among an operation mode of switching control of an electrostatic capacitance detection device according to comparison, a timing of an increase in the electrostatic capacitance of an electrostatic capacitance sensor, and a timing of determination
Figure 6B:
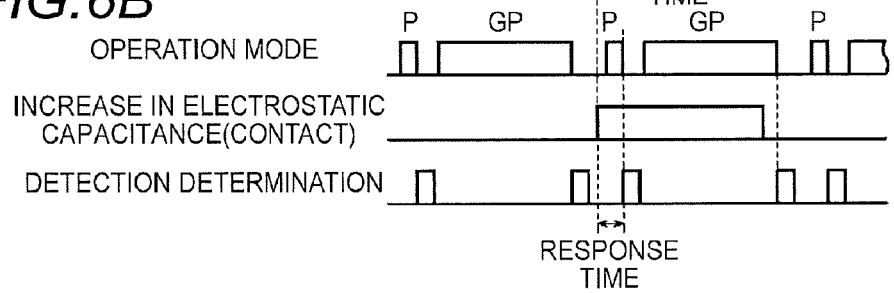
FIG. 6B is a diagram illustrating a relation among an operation mode of switching control of the electrostatic capacitance detection device according to the embodiment, a timing of an increase in electrostatic capacitance of the electrostatic capacitance sensor, and a timing of determination.

An operational effect when the control unit 13 alternately performs the switching control of the low-resolution detection mode and the switching control of the high-resolution detection mode will be described with reference to FIGS. 6A and 6B. In FIGS. 6A and 6B, a period in which the switching control of the low-resolution detection mode is performed is denoted by "P". A period in which the switching control of the high-resolution detection mode is performed is denoted by "GP".

FIG. 6A illustrates determination timings of the detection determination performed by the control unit 13 when the control unit 13 performs only the switching control of the high-resolution detection mode. This control is a comparison example of the switching control illustrated in FIG. 6B. FIG. 6B illustrates determination timings of the detection determination performed by the control unit 13 when the control unit 13 alternately performs the switching control of the low-resolution detection mode and the switching control of the high-resolution detection mode.

After the switching control ends, the control unit 13 determines presence or absence of contact of an object to the electrostatic capacitance sensor 10 based on a number-of-timings difference which can be obtained in the switching control.

When the control unit 13 performs only the switching control of the high-resolution detection mode, as illustrated in FIG. 6A, the control unit 13 outputs a determination result at the same period as a period of the switching control (for example, a determination result of the presence or absence of contact or approach of an object). Therefore, an average time of response times from a time point at which the object comes into contact with the electrostatic capacitance sensor 10 to a time point at which the control unit 13 determines that the object comes into contact with the electrostatic capacitance sensor 10 is a time which is the same or close to the period of the switching control.

Conversely, when the control unit 13 alternately performs the switching control of the low-resolution detection mode and the switching control of the high-resolution detection mode, as illustrated in FIG. 6B, the control unit 13 can output determination results at both of the period of the switching control of the low-resolution detection mode and the period of the switching control of the high-resolution detection mode. Therefore, the average time of response times from the time point at which the object comes into contact with the electrostatic capacitance sensor 10 to the time point at which the control unit 13 determines that the object comes into contact with the electrostatic capacitance sensor 10 is a value which is an average of both the periods or is close to the average of both of the periods. That is, when the control unit 13 alternately performs the switching control of the low-resolution detection mode and the switching control of the high-resolution detection mode, the control unit 13 can detect contact of an object in a shorter time on the average compared to a case in which only the switching control of the high-resolution detection mode is performed.

In order to further shorten the average of the response times necessary to detect contact of an object, a ratio of the number of switching controls performed in the low-resolution detection mode to the number of switching controls performed in the high-resolution detection mode may be increased in an execution pattern of the switching control of the low-resolution detection mode and the switching control of the high-resolution detection mode. Thus, it is possible to shorten the average of the response times.

Hereinafter, advantages of the electrostatic capacitance detection device 2 will be described.

(1) The electrostatic capacitance detection device 2 according to the present embodiment includes the electrostatic capacitance sensor 10 and the control device 11 controlling the electrostatic capacitance sensor 10. The control device 11 has a plurality of detection modes for detecting a capacitance change amount (an amount corresponding to a change amount of the electrostatic capacitance of the electrostatic capacitance sensor 10). The control device 11 detects a capacitance change amount in each of the plurality of detection modes and determines presence or absence of contact or approach of an object to the electrostatic capacitance sensor 10 based on the capacitance change amount. In such a configuration, the electrostatic capacitance detection device 2 can detect a plurality of change modes in which phases are different in a change in electrostatic capacitance.

(2) In the foregoing embodiment, the control device 11 has the high-resolution detection mode and the low-resolution detection mode as the detection modes for detecting the number-of-switchings difference $\Delta N$ (the capacitance change amount). Therefore, the determination of high resolution and the determination of low resolution can be performed when contact or approach of the object to the electrostatic capacitance sensor 10 is determined.

(3) In the foregoing embodiment, the control device 11 determines whether an object is in the contact state indicating the state in which the object is in contact with the electrostatic capacitance sensor 10 based on the number-of-switchings difference $\Delta Nb$ (the capacitance change amount) detected in the low-resolution detection mode. In such a configuration, it is possible to shorten a time necessary for determination when presence or absence of contact or approach of an object to the electrostatic capacitance sensor 10 is determined, compared to a case in which a contact state of an object is determined based on the number-of-switchings difference $\Delta Na$ (the capacitance change amount) detected in the high-resolution detection mode.

(4) In the foregoing embodiment, the control device 11 determines whether an object is in an approach state in which the object is not in contact with the electrostatic capacitance sensor 10 and is approaching the electrostatic capacitance sensor 10 based on the number-of-switchings difference $\Delta Na$ (the capacitance change amount) detected in the high-resolution detection mode.

In such a configuration, since the approach mode of an object coming into contact with or approaching the electrostatic capacitance sensor 10 is determined based on the number-of-switchings difference $\Delta Nb$ (the capacitance change amount) detected in the high-resolution detection mode, the approach state can be determined with high precision. That is, it is possible to suppress erroneous determination in which a different state from the approach state is determined to be the approach state or a state is conversely determined not to be the approach state when the state is the approach state.

(5) In the foregoing embodiment, the standard capacitor CS connected to the electrostatic capacitance sensor 10 in series is included. When the standard capacitor CS and the electrostatic capacitance sensor 10 at a first time are intermittently connected, the number of switchings (N1) until the middle potential VM between the standard capacitor CS and the electrostatic capacitance sensor 10 reaches the set potential Vth from an initial potential is detected as the first number of switchings (first number of connections). When the standard capacitor CS and the electrostatic capacitance sensor 10 at a second time distant from the first time by a predetermined time are intermittently connected, the number of switchings (N2) until the middle potential VM between the standard capacitor CS and the electrostatic capacitance sensor 10 reaches the set potential Vth from the initial potential is detected as the second number of switchings (second number of connections). Then, the capacitance change amount is derived as the number-of-switchings difference $\Delta N$ (number-of-times difference) which is a difference between the first number of switchings and the second number of switchings. The first time is "a time point before calculation of the number-of-switchings difference $\Delta N$" described in the embodiment and the second time is a "time point of calculation of the number-of-switchings difference $\Delta N$" described in the embodiment.

In this configuration, a change amount of the electrostatic capacitance (that is, a capacitance change amount) of the electrostatic capacitance sensor 10 is detected as a digital value. Therefore, calculation in which the change amount of the electrostatic capacitance of the electrostatic capacitance sensor 10 is used can be simple.

(6) In the foregoing embodiment, the standard capacitor CS is configured to include the plurality of sub-capacitors CS1 and CS2. The control device 11 has at least two modes in which the electrostatic capacitances of the standard capacitor CS are different as the capacitance coupling modes of the plurality of sub-capacitors CS1 and CS2. In the high-resolution detection mode, the control device 11 couples the plurality of sub-capacitors CS1 and CS2 in a first coupling mode and detects the capacitance change amount. In the low-resolution detection mode, the control device 11 couples the plurality of sub-capacitors CS1 and CS2 in a second coupling mode in which the electrostatic capacitance of the standard capacitor CS is less than the first coupling mode and detects the capacitance change amount. In the embodiment, the first coupling mode is a mode in which the first sub-capacitor CS1 and the second sub-capacitor CS2 are coupled in parallel. In the embodiment, the second coupling mode is a mode in which the second sub-capacitor CS2 is electrically isolated from the first sub-capacitor CS1 and only the first sub-capacitor CS1 is connected to the first circuit unit 12A.

In this configuration, the electrostatic capacitance of the standard capacitor CS is changed according to the coupling mode of the sub-capacitors CS1 and CS2. Then, the resolution of detection of the change amount of the electrostatic capacitance (that is, the capacitance change amount) of the electrostatic capacitance sensor 10 is allowed to be different by changing the electrostatic capacitance of the standard capacitor CS. In this way, in the foregoing configuration, a structure for changing the resolution of the detection is simple.

Second Embodiment

A circuit configuration of an electrostatic capacitance detection device 2 according to the present embodiment conforms to the circuit configuration of the electrostatic capacitance detection device 2 according to the first embodiment. Further, in the present embodiment, the following configuration is included. A control unit 13 controls times of closed states of the second switch SW2 and a third switch SW3 in a low-resolution detection mode.

Specifically, the control unit 13 controls the second switch SW2 and the third switch SW3 in two modes in which a closed time (a time in which the closed state is maintained) is different. The closed time of the second switch SW2 is the same as the closed time of the third switch SW3. Hereinafter, control performed to maintain the second switch SW2 and the third switch SW3 in a closed state for a predetermined time (hereinafter referred to as a "first time") is referred to as first opening and closing control. Further, control performed to control the second switch SW2 and the third switch SW3 to the closed state for a predetermined time (hereinafter referred to as a "second time") shorter than the first time is referred to as second opening and closing control.

The control unit 13 performs switching control of two modes as switching control of the low-resolution detection mode.

In the first switching control, the second switch SW2 and the third switch SW3 are controlled through the first opening and closing control. In the second switching control, the second switch SW2 and the third switch SW3 are controlled through the second opening and closing control.

The control unit 13 calculates a ratio of the number-of-switchings difference $\Delta N$ obtainable in the first switching control to the number-of-switchings difference $\Delta N$ obtainable in the second switching control (a number-of-switchings difference obtainable in the first switching control/a number-of-switchings difference obtainable in the second switching control: which is hereinafter referred to as a "number-of-switchings difference ratio").

The number-of-switchings difference ratio is different according to the kind of object in contact with the electrostatic capacitance sensor 10. In a case in which a person is in contact with or is approaching the electrostatic capacitance sensor 10, 1 or a value close to 1 is obtained. On the other hand, in a case in which water is in contact with or is approaching the electrostatic capacitance sensor 10, value distant from 1 is obtained. This is due to the following reason.

At contact of a person to the electrostatic capacitance sensor 10, the electrostatic capacitance of the electrostatic capacitance sensor 10 is considerably increased than at contact of water. That is, in contact of a person, a time constant of a sensor capacitor CX is less than in attachment of water. Therefore, in the case of contact of a person, the middle potential VM decreases by a substantial given value irrespective of a time length of the closed state of the second switch SW2 and the third switch SW3. Accordingly, the number-of-switchings difference ratio is a value close to 1. In contrast, in attachment of water, an effect of reducing the time constant of the sensor capacitor CX is less than in contact of a person. In the case of contact of water, a reduction width of the middle potential VM is smaller as the time length of the closed state of the second switch SW2 and the third switch SW3 is shorter. As a result, when the time length of the closed state of the second switch SW2 and the third switch SW3 is short, a time in which the middle potential VM reaches the set potential Vth from the initial potential is lesser shortened than in a case in which the time length is long. Thus, a decrease amount of the number of switchings N is also small, and thus the number-of-switchings difference $\Delta N$ decreases. As a result, the number-of-switchings difference ratio is greater than 1. A difference in the number-of-switchings difference (the number-of-switchings difference obtainable in the first switching control–the number-of-switchings difference obtainable in the second switching control) indicates the same characteristics as the number-of-switchings difference ratio. That is, the difference in the number-of-switchings difference differs according to a kind of object in contact with the electrostatic capacitance sensor 10.

Using the fact that the difference in the number-of-switchings difference differs according to a kind of object, the control unit 13 determines a kind of the object which is in contact with the electrostatic capacitance sensor 10 based on whether the number-of-switchings difference ratio (the number-of-switchings difference obtainable in the first switching control/the number-of-switchings difference obtainable in the second switching control) or the difference in the number-of-switchings difference (the number-of-switchings difference obtainable in the first switching control–the number-of-switchings difference obtainable in the second switching control) is greater than a predetermined value.

Figure 7:
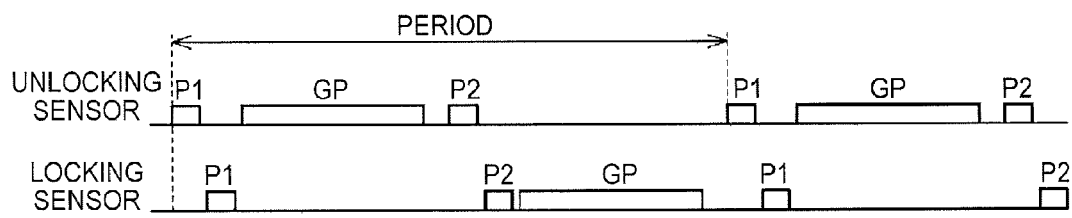
FIG. 7 is a timing chart illustrating an operation example in control of the low-resolution detection mode and control of the high-resolution detection mode.

FIG. 7 illustrates an example of a timing chart of the first switching control of the low-resolution detection mode, the second switching control of the low-resolution detection mode, and the switching control of the high-resolution detection mode. "P1" illustrated in FIG. 7 indicates the first switching control of the low-resolution detection mode. "P2" indicates the second switching control of the low-resolution detection mode. "GP" indicates the switching control of the high-resolution detection mode. As illustrated in FIG. 7, in the embodiment, control is performed to obtain the number-of-switchings difference ratio in both of the unlocking sensor 10A and the locking sensor 10B. The control for obtaining the number-of-switchings difference ratio or the difference in the number-of-switchings difference may be performed in only one of the unlocking sensor 10A and the locking sensor 10B.

In the foregoing configuration, as described above, the kind of object can be determined based on the number-of-switchings difference ratio or the difference in the number-of-switchings difference when an object is in contact with or is approaching the electrostatic capacitance sensor 10. According to the number-of-switchings difference ratio or the difference in the number-of-switchings difference, the kind of object can be determined with predetermined precision irrespective of the magnitude of the resolution of the electrostatic capacitance detection device 2 when an object is in contact with or is approaching the electrostatic capacitance sensor 10.

Modification Example of Second Embodiment

A modification example of the second embodiment will be described with reference to FIG. 8.

In the present modification example, the control unit 13 controls, the time of the closed state of the second switch SW2 and the third switch SW3 in both of the low-resolution detection mode and the high-resolution detection mode. Thus, it is possible to obtain the number-of-switchings difference ratio (or the difference in the number-of-switchings difference) in the switching control of the low-resolution detection mode and it is possible to obtain the number-of-switchings difference ratio (or the difference in the number-of-switchings difference) in the switching control of the high-resolution detection mode. When the kind of object in contact with the electrostatic capacitance sensor 10 is determined accurately, the number-of-switchings difference ratio (or the difference in the number-of-switchings difference) obtainable in the switching control of the high-resolution detection mode is used. When the kind of object in contact with the electrostatic capacitance sensor 10 is determined quickly, the number-of-switchings difference ratio (or the difference in the number-of-switchings difference) obtainable in the switching control of the low-resolution detection mode is used.

Figure 8:
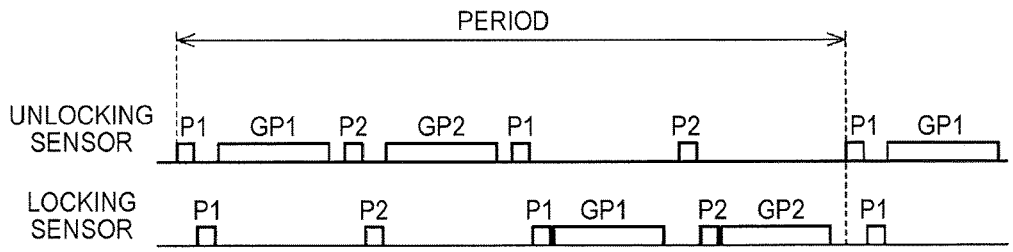
FIG. 8 is a timing chart illustrating another operation example in the control of the low-resolution detection mode and the control of the high-resolution detection mode.

FIG. 8 illustrates a timing chart of the first switching control of the low-resolution detection mode, the second switching control of the low-resolution detection mode, the first switching control of the high-resolution detection mode, and the second switching control of the high-resolution detection mode. "GP1" illustrated in FIG. 8 indicates the first switching control of the high-resolution detection mode. "GP2" indicates the second switching control of the high-resolution detection mode.

In the foregoing configuration, the advantages conforming to the second embodiment can be obtained. Since the number-of-switchings difference ratio or the difference in the number-of-switchings difference obtainable based on the first switching control of the high-resolution detection mode and the second switching control of the high-resolution detection mode is a value obtainable through the high-resolution detection, an object in which an increase amount of the electrostatic capacitance of the electrostatic capacitance sensor 10 is a value between a person and water can be determined to be distinguished from the person and the water.

Third Embodiment

A circuit configuration of the electrostatic capacitance detection device 2 according to the present embodiment conforms to the circuit configuration of the electrostatic capacitance detection device 2 according to the first embodiment. In the present embodiment, the circuit configuration according to the first embodiment will be assumed in the description. In a technology according to the present embodiment, the standard capacitor CS with a large capacity suffices and the standard capacitor CS may not be configured to include a plurality of sub-capacitors. As technologies according to the present embodiment, as described above in the first embodiment, the technology related to the switching control of the high-resolution detection mode and the technology for distinguishing non-detection, approach detection, and contact detection from each other based on the magnitude of the number-of-switchings difference ΔN and determining the presence or absence of contact or approach of an object to the electrostatic capacitance sensor 10 are used.

Figure 9A:
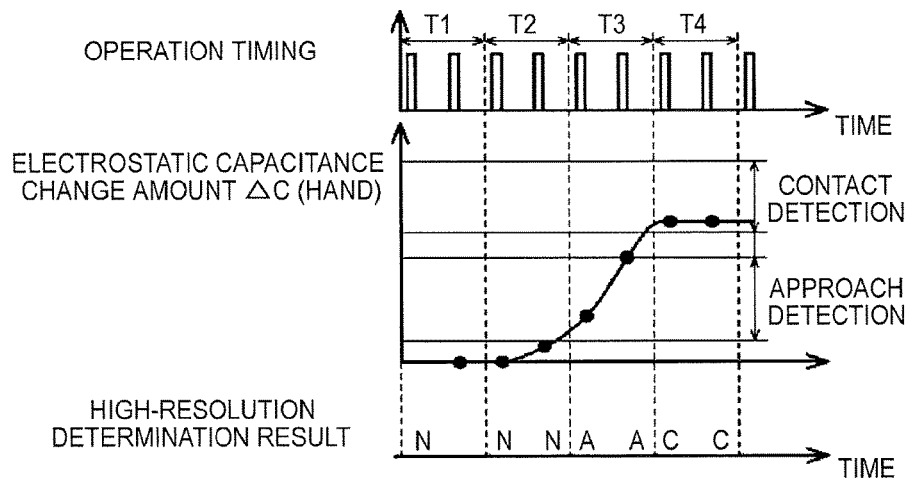
FIGS. 9A and 9B are diagrams illustrating a relation among an operation timing of the high-resolution detection mode, a transition of an electrostatic capacitance change amount of the electrostatic capacitance sensor, and a determination result at the time of contact of a hand to the electrostatic capacitance sensor and at the time of attachment of a water to the electrostatic capacitance sensor, respectively.
Figure 9B:
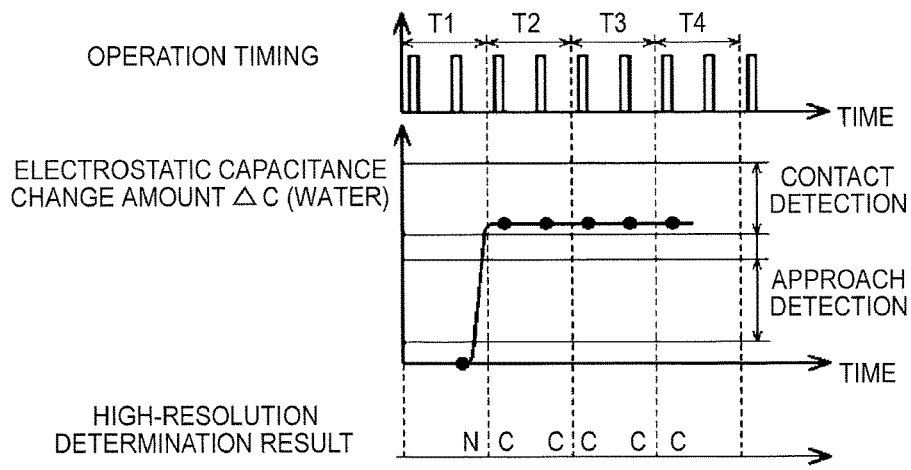

An object determination process through switching control of the high-resolution detection mode will be described with reference to FIGS. 9A to 10. FIG. 9A illustrates an example of a change in the electrostatic capacitance of the electrostatic capacitance sensor 10 when a hand is in contact with the electrostatic capacitance sensor 10. FIG. 9B illustrates an example of a change in the electrostatic capacitance of the electrostatic capacitance sensor 10 when water is attached to the electrostatic capacitance sensor 10.

As illustrated in FIGS. 9A and 9B, when water is attached to the electrostatic capacitance sensor 10, a capacitance change of the electrostatic capacitance of the electrostatic capacitance sensor 10 is faster than in a case in which a hand is in contact with the electrostatic capacitance sensor 10. In this way, the speed of the capacitance change of the electrostatic capacitance is different in accordance with contact to the electrostatic capacitance sensor 10. Using such a property, it is possible to determine a kind of object in contact with the electrostatic capacitance sensor 10.

FIGS. 9A and 9B illustrate timings of the switching control on graphs indicating a change in the electrostatic capacitance of the electrostatic capacitance sensor 10. A determination result in each switching control obtained through the object determination process (see FIG. 5A) in the high-resolution detection mode is shown below the graph. As illustrated in FIGS. 5A and 5B, change modes of the electrostatic capacitance at the time of approach and contact of an object to the electrostatic capacitance sensor 10 have unique patterns according to the object.

In the embodiment, using the fact that the change modes have the unique patterns, the kind of object in contact with and approaching the electrostatic capacitance sensor 10 is determined. Pattern 1 illustrated in FIG. 10 is a collation pattern used in a case in which it is determined whether a person or a hand is approaching and in contact with the electrostatic capacitance sensor 10. The collation pattern regulates determination content in each of first, second, third, and fourth periods which are continuous.

Pattern 2 illustrated in FIG. 10 is a collation pattern used in a case in which it is determined whether water is approaching and attached to the electrostatic capacitance sensor 10.

The control unit 13 periodically performs the switching control in the high-resolution detection mode and performs detection termination (determination of present or absence of contact or approach of an object based on the number-of-switchings difference ΔN) for each switching control. The control unit 13 stores the determination results in a chorological order or in association with a chronological parameter. The control unit 13 performs pattern collation at the time of determination of contact detection through the detection determination. For example, the control unit 13 compares a pattern of the determination result for a predetermined period to Pattern 1 and Pattern 2 which are collation patterns and determines which pattern is matched. In a case in which the pattern of the determination result for the predetermined time is matched with one pattern, it is determined that an object corresponding to collation pattern is determined to be in contact with the electrostatic capacitance sensor 10. When the pattern of the determination result for the predetermined period is not matched with any of the patterns, the pattern collation is performed again based on a pattern of a determination result which is obtained subsequently.

The advantages of the electrostatic capacitance detection device 2 according to the present embodiment will be described.

The control device 11 determines whether an object is in the contact state, the approach state, or the non-detection state based on each of a plurality of number-of-switchings differences (capacitance change amounts) continuously obtained in the high-resolution detection mode. Then, the kind of an object in contact with the electrostatic capacitance sensor 10 is determined based on a pattern of a determination result in each of the plurality of number-of-switchings differences (capacitance change amounts).

The change mode of the electrostatic capacitance of the electrostatic capacitance sensor 10 at the time of approach of an object to the electrostatic capacitance sensor 10 differs according to the kind of object. In the foregoing configuration, the change mode is detected as a pattern of a plurality of capacitance change amounts continuously obtained in the high-resolution detection mode. Then, the control device 11 determines the kind of object in contact with the electrostatic capacitance sensor 10 based on not only one piece of information (one capacitance change amount) but also a pattern of a plurality of pieces of information (a combination of the determination results of the capacitance change amounts). Therefore, it is possible to improve determination precision at the time of determination of the kind of object in contact with or approaching the electrostatic capacitance sensor 10. The technology of the present embodiment can be applied to detection of an object such as mist, sleet, snow, hail, or dust.

Fourth Embodiment

A circuit configuration of the electrostatic capacitance detection device 2 according to the present embodiment conforms to the circuit configuration of the electrostatic capacitance detection device 2 according to the first embodiment. In the present embodiment, the circuit configuration according to the first embodiment will be assumed in the description. In a technology according to the present embodiment, the standard capacitor CS with a large capacity suffices and the standard capacitor CS may not be configured to include a plurality of sub-capacitors. As technologies according to the present embodiment, as described above in the first embodiment, the technology related to the switching control of the high-resolution detection mode and the technology for distinguishing non-detection, approach detection, and contact detection from each other based on the magnitude of the number-of-switchings difference ΔN and determining the presence or absence of contact or approach of an object to the electrostatic capacitance sensor 10 are used.

A gesture determination process through switching control of the high-resolution detection mode will be described with reference to FIGS. 11A to 13.

FIGS. 11A and 11B illustrate examples of changes in the electrostatic capacitance of the electrostatic capacitance sensor 10 when a hand is moving from the side of the unlocking sensor 10A to the side of the locking sensor 10B near the electrostatic capacitance sensor 10 without contact to the electrostatic capacitance sensor 10.

As illustrated in FIGS. 11A and 11B, as a hand is approaching the unlocking sensor 10A, a change amount of the electrostatic capacitance of the unlocking sensor 10A increases. When the hand is approaching the unlocking sensor 10A most closely, the change amount of the electrostatic capacitance reaches a peak. Thereafter, as the hand becomes away from the unlocking sensor 10A, the change amount of the electrostatic capacitance of the unlocking sensor 10A decreases. When the hand is located between the unlocking sensor 10A and the locking sensor 10B, the change amount of the electrostatic capacitance is "0" or a value close to "0" on both sides. Thereafter, as the hand is continuously approaching the locking sensor 10B, the change amount of the electrostatic capacitance of the locking sensor 10B increases. When the hand is approaching the locking sensor 10B most closely, the change amount of the electrostatic capacitance reaches a peak. Thereafter, as the hand becomes away from the locking sensor 10B, the change amount of the electrostatic capacitance of the locking sensor 10B decreases.

An operation (gesture) of the hand moving from the unlocking sensor 10A to the locking sensor 10B can be ascertain as chronological changes of the change amount of the electrostatic capacitance of the unlocking sensor 10A and the change amount of the electrostatic capacitance of the locking sensor 10B. That is, a predetermined gesture can be detected based on a pattern of the change amounts of the electrostatic capacitance of the unlocking sensor 10A and the locking sensor 10B.

In FIGS. 11A and 11B, timings of the switching control are shown above graphs indicating changes in the electrostatic capacitance of the electrostatic capacitance sensors 10. Further, determination results of each switching control obtained through the object determination process (see FIG. 5A) in the high-resolution detection mode are shown below the graphs. In this way, change modes of the electrostatic capacitance when a predetermined gesture from the unlocking sensor 10A to the locking sensor 10B is performed have unique patterns. In the present embodiment, using the fact that the change modes have the unique patterns, a predetermined gesture from the unlocking sensor 10A to the locking sensor 10B is detected.

Patterns illustrated in FIG. 12 are collation patterns used in a case in which whether a gesture is a predetermined gesture is determined.

The control unit 13 periodically performs the switching control in the high-resolution detection mode in regard to each of the unlocking sensor 10A and the locking sensor 10B and performs detection determination (determination of present or absence of contact or approach of an object based on the number-of-switchings difference ΔN) for each switching control. The control unit 13 stores the determination results in a chorological order or in association with a chronological parameter. Then, the control unit 13 performs pattern collation between patterns of the determination results obtained in this way and the collation patterns corresponding to the predetermined gesture. For example, the control unit 13 compares the patterns of the determination results (including the determination results of the unlocking sensor 10A and the locking sensor 10B) for a predetermined period to the collation patterns to determine whether both of the patterns are matched. In a case in which the pattern of the determination result for the predetermined period is matched to the collation pattern, the control unit 13 determines that the predetermined gesture is performed.

The technology according to the present embodiment can be applied not only to a gesture of moving a hand from the unlocking sensor 10A to the locking sensor 10B but also to detection of various gestures. For example, the present technology can be applied to detection of a gesture of moving a hand in an opposite direction to the foregoing gesture, a gesture of holding both hands up to the unlocking sensor 10A and the locking sensor 10B, and a gesture of repeating a reciprocation operation of approaching a hand and separating the hand from the unlocking sensor 10A or the locking sensor 10B twice or more.

Figure 13:
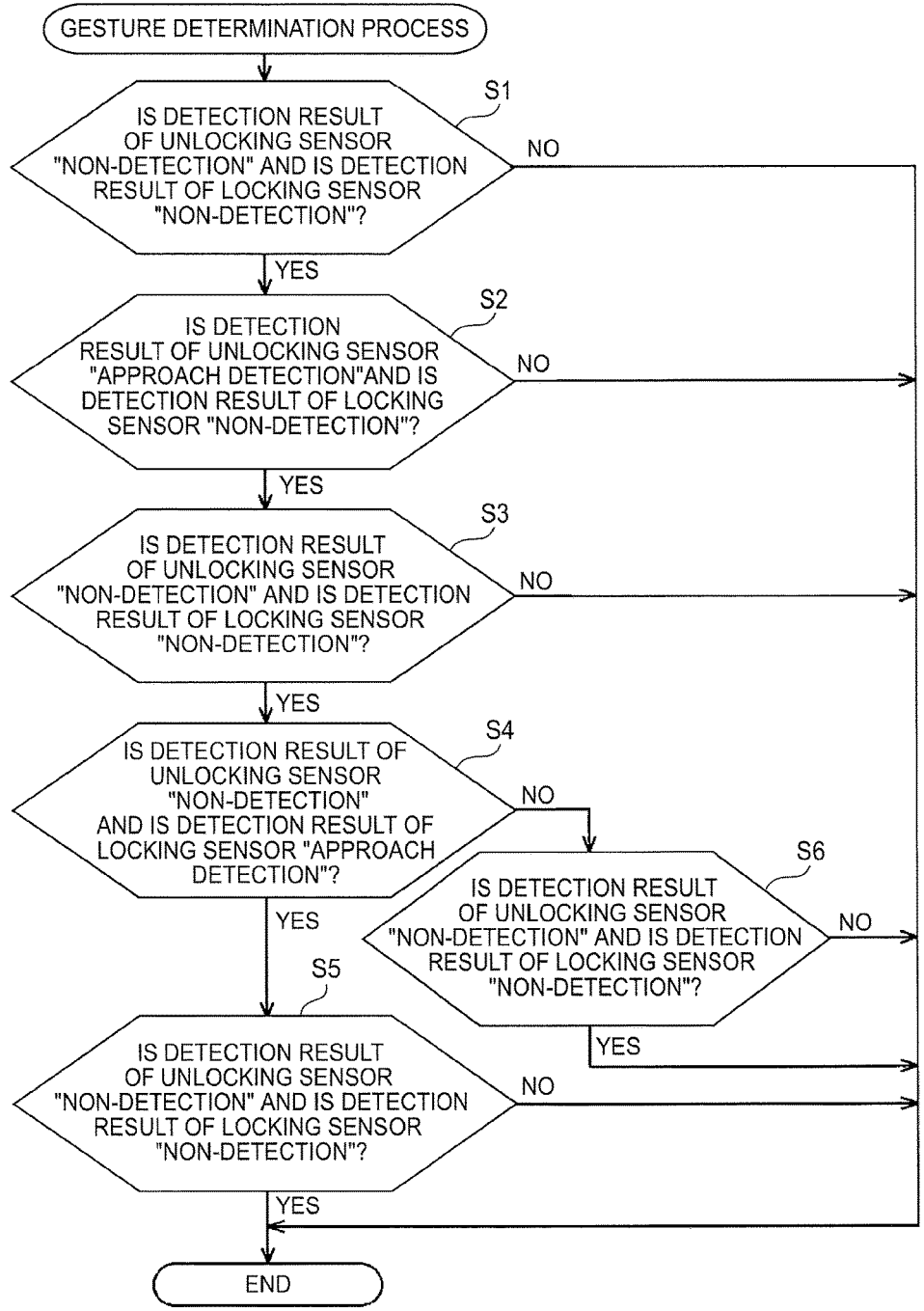
FIG. 13 is a flowchart illustrating a gesture determination process.

FIG. 13 is a flowchart illustrating a process of determining a gesture (hereinafter referred to as a "gesture determination process"). The gesture determination process corresponds to the table of FIG. 12. The control unit 13 performs a series of processes of subsequent steps S1 to S5 at a predetermined period. The control unit 13 performs the switching control in the high-resolution detection mode in each of the unlocking sensor 10A and the locking sensor 10B in each step to obtain a determination result of each of both the sensors 10A and 10B.

In step S1, the control unit 13 determines whether all of the determination results obtainable for a first period are "non-detection" in the unlocking sensor 10A and the locking sensor 10B. When the determination is positive, that is, all of the determination results are "non-detection", the process proceeds to step S2.

In step S2, the control unit 13 determines whether at least one or more (for example, three) determination results obtainable for a second period are continuously "approach detection" in the unlocking sensor 10A and all of the determination results obtainable for the second period are "non-detection" in the locking sensor 10B. When this determination is positive, the process proceeds to step S3.

In step S3, the control unit 13 determines whether at least one or more (for example, seven) determination results obtainable for a third period are continuously "non-detection" in the unlocking sensor 10A and the locking sensor 10B. When the determination is positive, the process proceeds to step S4.

In step S4, the control unit 13 determines whether at least one or more (for example, three) determination results obtainable for a fourth period are continuously "approach detection" in the locking sensor 10B and all of the determination results obtainable for the fourth period are "non-detection" in the unlocking sensor 10A. When the determination is positive, the process proceeds to step S5.

In step S5, the control unit 13 determines whether all of the determination results obtainable for a fifth period are "non-detection" in the unlocking sensor 10A and the locking sensor 10B. When the determination is positive, that is, all of the determination results are "non-detection", a "slide gesture" is determined to be performed.

When the determination of step S4 is negative, the process proceeds to step S6. In step S6, the control unit 13 determines whether all of the determination results obtainable for the fourth period are "non-detection" in the unlocking sensor 10A and the locking sensor 10B. When the determination is positive, "the gesture of holding the hand up to the unlocking sensor 10A" is determined to be performed.

When the determination is performed in steps S1, S2, S3, S5, and S6, the control unit 13 ends the gesture determination process once. Thereafter, the gesture determination process is performed again after a predetermined time passes.

Hereinafter, advantages of the electrostatic capacitance detection device 2 according to the embodiment will be described.

In the present embodiment, the electrostatic capacitance detection device 2 includes the unlocking sensor 10A (first electrostatic capacitance sensor) and the locking sensor 10B (second electrostatic capacitance sensor). The unlocking sensor 10A and the locking sensor 10B are disposed to be distant by a setting distance.

The control device 11 detects the number-of-switchings difference (the capacitance change amount) in each of the unlocking sensor 10A and the locking sensor 10B and determines one of the contact state, the approach state, and the non-detection state based on the capacitance change amount. A motion of an object approaching the unlocking sensor 10A and the locking sensor 10B is detected based on a pattern of an overall determination result including the determination result of the unlocking sensor 10A and the determination result of the locking sensor 10B obtained during the same period. In such a configuration, it is possible to detect a gesture of moving a hand near the electrostatic capacitance detection device 2.

Fifth Embodiment

Figure 14:
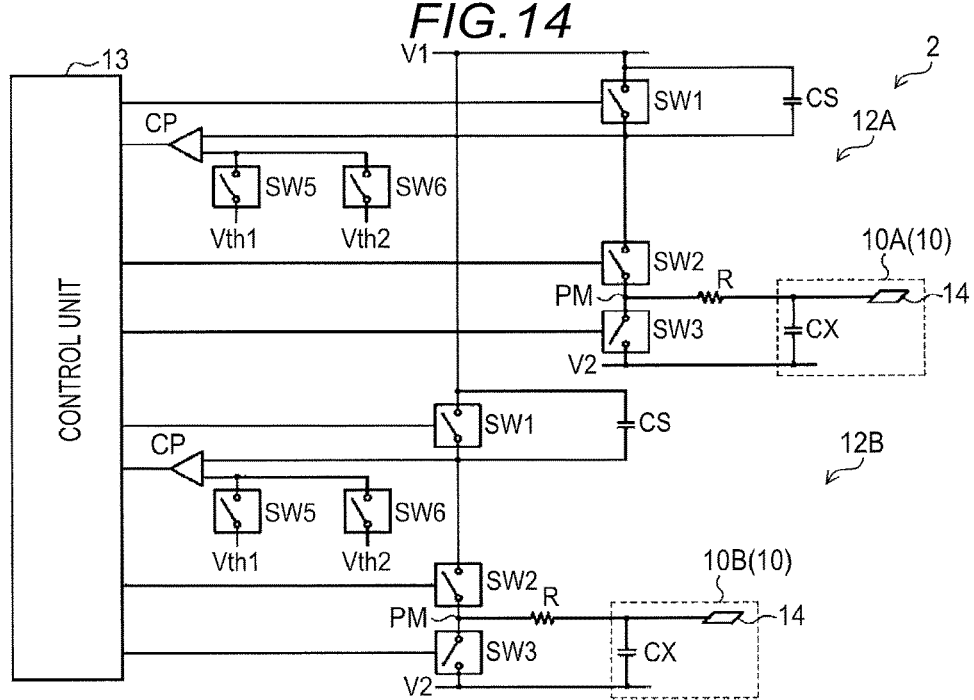
FIG. 14 is a circuit diagram illustrating an electrostatic capacitance detection device.

An electrostatic capacitance detection device 2 according to a fifth embodiment will be described with reference to FIG. 14. The electrostatic capacitance detection device 2 according to the present embodiment is different from the electrostatic capacitance detection device 2 with the basic configuration in the following points.

In the basic configuration of the electrostatic capacitance detection device 2, it is determined in the switching control whether the middle potential VM is less than the set potential Vth. In contrast, the electrostatic capacitance detection device 2 according to the present embodiment has a first mode in which it is determined whether the middle potential VM is less than a first set potential Vth1 and a second mode in which it is determined whether the middle potential VM is less than a second set potential Vth2. The second set potential Vth2 is a higher potential than the first set potential Vth1.

The potential determination device CP is configured to include a comparator. A standard potential of the potential determination device CP can be switched to one of the first set potential Vth1 and the second set potential Vth2 through operations of a fifth switch SW5 and a sixth switch SW6. Specifically, a potential source of the first set potential Vth1 and a potential source of the second set potential Vth2 are connected to an input unit (a unit to which the standard potential is input) of the potential determination device CP. The fifth switch SW5 is disposed between the input unit and the potential source of the first set potential Vth1 and a sixth switch SW6 is disposed between the input unit and the potential source of the second set potential Vth2.

The control unit 13 switches a potential to be input to the input unit to one of the first set potential Vth1 and the second set potential Vth2 through operations of the fifth switch SW5 and the sixth switch SW6. The potential to be input to the input unit corresponds to the set potential Vth serving as a standard of the comparison of the middle potential VM.

In a case in which the set potential Vth is high, a time in which the potential of the middle position PM reaches the set potential Vth from the initial potential in the foregoing switching control is short. Therefore, the control unit 13 has the characteristics in which a period at which the number of switchings N is obtained is short. On the other hand, when a change amount of the electrostatic capacitance of the electrostatic capacitance sensor 10 is small, it is difficult to detect the change amount as the number-of-switchings difference $\Delta N$ because of the characteristics in which the time in which the potential of the middle position PM reaches the set potential Vth from the initial potential is short. That is, in a case in which the set potential Vth is high, a change in the electrostatic capacitance of the electrostatic capacitance sensor 10 is detected at low resolution.

In a case in which the set potential Vth is low, a time in which the potential of the middle position PM reaches the set potential Vth from the initial potential in the foregoing switching control is long. Therefore, the control unit 13 has the characteristics in which a period at which the number of switchings N is obtained is long. On the other hand, when a change amount of the electrostatic capacitance of the electrostatic capacitance sensor 10 is small, the change amount can be detected as the number-of-switchings difference $\Delta N$ because of the characteristics in which the time in which the potential of the middle position PM reaches the set potential Vth from the initial potential is long. That is, in a case in which the set potential Vth is low, a change in the electrostatic capacitance of the electrostatic capacitance sensor 10 is detected at high resolution.

The control unit 13 has two detection modes utilizing the characteristics of the case in which the set potential Vth is high and the characteristics of the case in which the set potential Vth is low. That is, the control unit 13 has a high-resolution detection mode and a low-resolution detection mode.

In the high-resolution detection mode, the control unit 13 sets the standard potential with respect to the middle potential VM to the first set potential Vth1 (low potential) by controlling the fifth switch SW5 to the closed state and controlling the sixth switch SW6 to the open state, and detects the capacitance change amount of the electrostatic capacitance sensor 10 at high resolution. Thus, the control unit 13 detects a state in which an object is approaching the electrostatic capacitance sensor 10 and is not in contact with the electrostatic capacitance sensor 10 (that is, an approach state) with high precision.

In the low-resolution detection mode, the control unit 13 sets the standard potential with respect to the middle potential VM to the second set potential Vth2 (high potential) by controlling the fifth switch SW5 to the open state and controlling the sixth switch SW6 to the closed state, and detects the capacitance change amount of the electrostatic capacitance sensor 10 at low resolution. Thus, the control unit 13 can obtain the capacitance change amount at a short period and achieves a determination result of whether an object is in contact with or approaching the electrostatic capacitance sensor 10 in a short time.

Execution modes of the switching operation of the high-resolution detection mode and the switching operation of the low-resolution detection mode in the control unit 13 conform to the execution modes of the first embodiment. For example, alternately performing the switching operation of the high-resolution detection mode and the switching operation of the low-resolution detection mode, obtaining the number-of-switchings difference $\Delta N$ in each switch operation, and determining contact or approach of an object to the electrostatic capacitance sensor 10 based on the number-of-switchings difference $\Delta N$ conform to the execution modes of the first embodiment.

As described above, the characteristics of the switching operation of the high-resolution detection mode and the characteristics of the switching operation of the low-resolution detection mode are the same as the characteristics of the modes described in the first embodiment. Therefore, in the present embodiment, it is possible to obtain the advantages conforming to the advantages of the first embodiment.

The advantages of the electrostatic capacitance detection device 2 according to the present embodiment will be described.

In the present embodiment, the set potential Vth at the time of detection of the number of connections until the middle potential VM reaches the set potential Vth from the initial potential as the first number of connections or the second number of connections can be configured to be settable. The control device 11 sets the set potential Vth to the first set potential Vth1 and detects the capacitance change amount in the high-resolution detection mode, and sets the set potential Vth to the second set potential Vth2 higher than the first set potential Vth1 and detects the capacitance change amount in the low-resolution detection mode.

In this configuration, the resolution of detection of the change amount of the electrostatic capacitance (that is, the capacitance change amount) of the electrostatic capacitance sensor 10 is set to be different by changing the value of the foregoing set potential Vth. In this way, in the foregoing configuration, a structure for changing the resolution of the detection is simple.

In this configuration, the configuration of the standard capacitor CS is simpler than that of the electrostatic capacitance detection device 2 according to the first embodiment. The configuration of the standard capacitor CS may be configured to include a plurality of sub-capacitors as in the first embodiment and the standard potential of the potential determination device CP may be switched according to the coupling mode of the sub-capacitors as in the fifth embodiment.

Modification Example of Fifth Embodiment

Figure 15:
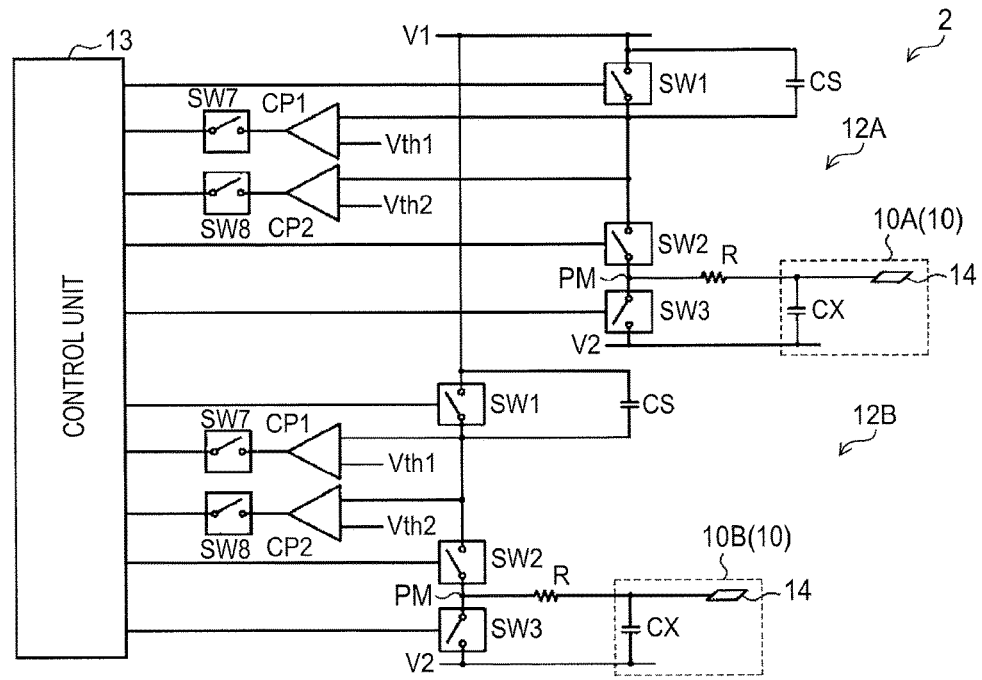
FIG. 15 is a circuit diagram illustrating an electrostatic capacitance detection device.

A modification example of the fifth embodiment will be described with reference to FIG. 15.

An electrostatic capacitance detection device 2 according to the present modification example has a first mode in which it is determined whether the middle potential VM is less than the first set potential Vth1 and a second mode in which it is determined whether the middle potential VM is less than the second set potential Vth2. This point is the same as that of the fifth embodiment. The present modification example is different from the fifth embodiment in means for switching between the first set potential Vth1 and the second set potential Vth2.

In the present modification example, the electrostatic capacitance detection device 2 has two potential determination devices CP (hereinafter referred to as a first potential determination device CP1 and a second potential determination device CP2). A seventh switch SW7 is set up between an output unit of the first potential determination device CP1 and the control unit 13 and an eighth switch SW8 is set up between an output unit of the second potential determination device CP2 and the control unit 13. A standard potential of the first potential determination device CP1 is set to the first set potential Vth1. A standard potential of the second potential determination device CP2 is set to the second set potential Vth2 which is a higher potential than the first potential.

In such a configuration, control of the seventh switch SW7 and the eighth switch SW8 conforms to the control of the fifth switch SW5 and the sixth switch SW6 in the fifth embodiment. That is, the control unit 13 detects the capacitance change amount of the electrostatic capacitance sensor 10 at high resolution by controlling the seventh switch SW7 to the closed state and controlling the eighth switch SW8 to the open state. The control unit 13 detects the capacitance change amount of the electrostatic capacitance sensor 10 at low resolution by controlling the eighth switch SW8 to the closed state and controlling the seventh switch SW7 to the open state. That is, in the present modification example, the electrostatic capacitance detection device 2 is the same as the electrostatic capacitance detection device 2 according to the fifth embodiment in that the set potential Vth is switched. Therefore, in the electrostatic capacitance detection device 2 according to the present modification example, it is possible to obtain the advantages conforming to the advantages of the electrostatic capacitance detection device 2 according to the fifth embodiment.

Other Embodiments

In the foregoing embodiments, the control unit 13 can perform water processing to be described below in addition to each control and process described above.

Figure 16:
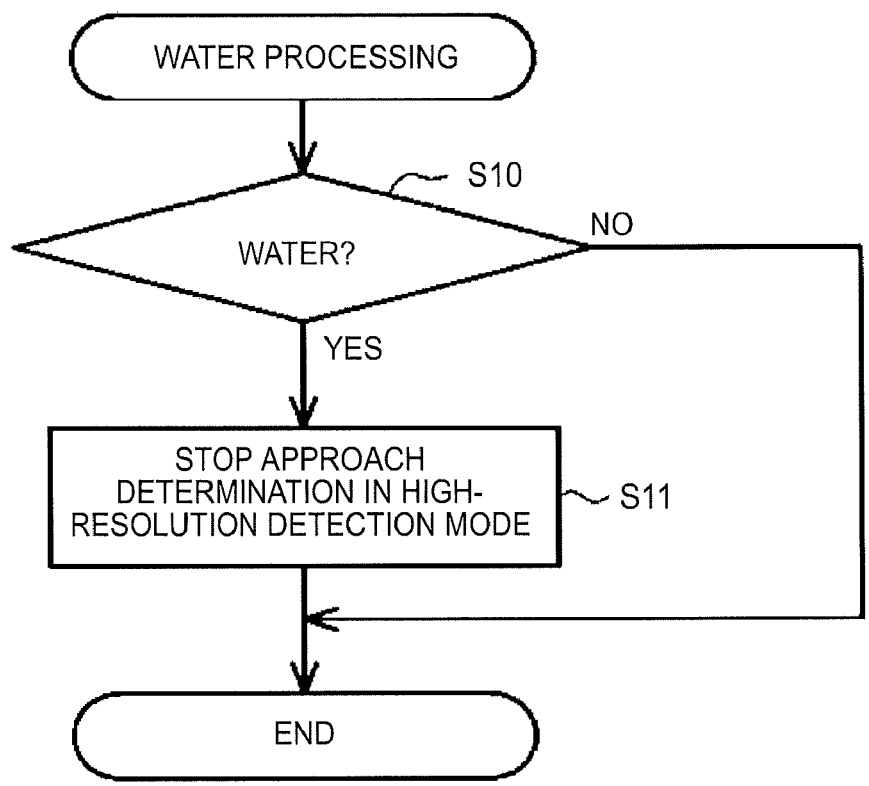
FIG. 16 is a flowchart illustrating water processing.

As illustrated in FIG. 16, the control unit 13 determines the kind of object in contact with or approaching the electrostatic capacitance sensor 10 based on a pattern of determination results (step S10). In step S10, the switching control and the object determination process described in the second or third embodiment are performed.

When the control unit 13 determines that an object is water in step S10 (determined to be "water"), the control unit 13 stops determination (approach determination) to determine an approach state of an object based on the number-of-switchings difference ΔN obtained from the switching control in the high-resolution detection mode (step S11).

When the water is attached to the electrostatic capacitance sensor 10 (or attached to a cover near the electrostatic capacitance sensor 10), the following occurs. That is, the electrostatic capacitance of the electrostatic capacitance sensor 10 is changed due to a change in the amount of water or the size of an area in which the water is attached or the like. Therefore, the determination precision at the time of determination of an approach state of an object deteriorates. In the foregoing configuration, the determination based on the high-resolution detection mode is stopped when an object in contact with the electrostatic capacitance sensor 10 or an object approaching the electrostatic capacitance sensor 10 is determined to be water. That is, the electrostatic capacitance detection device 2 does not output a determination result with low precision.

In the foregoing embodiments, the electrostatic capacitance detection device 2 is contained in the door handle 1, but the disposition location of the electrostatic capacitance detection device 2 is not limited thereto. For example, the electrostatic capacitance detection device 2 can be disposed inside a vehicle door, a vehicle (for example, a vicinity of a platform), a window pillar (inside a pillar) of a vehicle, or an emblem of a vehicle.

(1) An electrostatic capacitance detection device according to an aspect of this disclosure includes an electrostatic capacitance sensor and a control device that controls the electrostatic capacitance sensor. The control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount. The electrostatic capacitance detection device with the foregoing configuration can detect the plurality of change modes in which phases are different in a change in the electrostatic capacitance.

(2) In the electrostatic capacitance detection device, the control device may have a high-resolution detection mode and a low-resolution detection mode in which resolution of detection of the electrostatic capacitance is different, as the plurality of detection modes. In this configuration, determination of high precision and determination of low precision can be performed when contact or approach of the object to the electrostatic capacitance sensor is determined.

(3) In the electrostatic capacitance detection device, based on the capacitance change amount detected in the low-resolution detection mode, the control device may determine whether an object is in a contact state indicating a state in which the object is in contact with the electrostatic capacitance sensor. In this configuration, it is possible to shorten a time necessary for determination when the presence or absence of the contact or approach of the object to the electrostatic capacitance sensor more than in a case in which a contact state of an object is determined based on the capacitance change amount detected in the high-resolution detection mode.

(4) In the electrostatic capacitance detection device, based on the capacitance change amount detected in the high-resolution detection mode, the control device may determine whether the object is in an approach state which is a state in which the object is not in contact with the electrostatic capacitance sensor and a state in which the object is approaching the electrostatic capacitance sensor. Here, the "approach state which is the state in which the object is approaching" includes a state in which the object is approaching (a state in which an approach operation to the object is continuous) and an approach state (a state in which the approach operation is completed or a state in which the object is stopped at a distance from the electrostatic capacitance sensor or is in the vicinity of the electrostatic capacitance sensor without being stopped).

In this configuration, since the approach mode of the object in contact with or approaching the electrostatic capacitance sensor is determined based on the capacitance change amount detected in the high-resolution detection mode, it is possible to determine the approach state with high precision.

(5) In the electrostatic capacitance detection device, the control device may determine whether the object is in the contact state indicating the state in which the object is in contact with the electrostatic capacitance sensor, the approach state indicating a state in which the object is not in contact with the electrostatic capacitance sensor and a state in which the object is approaching the electrostatic capacitance sensor, or a non-detection state indicating a state in which the object does not approach the electrostatic capacitance sensor in each of a plurality of the capacitance change amounts obtained continuously in the high-resolution detection mode, and determine a kind of object in contact with the electrostatic capacitance sensor based on a pattern of determination results in the plurality of capacitance change amounts. Here, the "approach state which is the state in which the object is approaching" includes a state in which the object is approaching (a state in which an approach operation to the object is continuous) and an approach state (a state in which the approach operation is completed or a state in which the object is stopped at a distance from the electrostatic capacitance sensor or is in the vicinity of the electrostatic capacitance sensor without being stopped).

The change mode of the electrostatic capacitance of the electrostatic capacitance sensor at the time of approach of the object to the electrostatic capacitance sensor differs according to the kind of object. In the foregoing configuration, the change mode is detected as a pattern of the plurality of capacitance change amounts obtained continuously in the high-resolution detection mode. Then, the control device determines the kind of object in contact with the electrostatic capacitance sensor based on not only one piece of information (one capacitance change amount) but also a pattern (combination) of a plurality of pieces of information. Therefore, in regard to the object in the contact with or approaching the electrostatic capacitance sensor, it is possible to improve determination precision when the kind of object is determined.

(6) In the electrostatic capacitance detection device, when a determination result when the object in contact with the electrostatic capacitance sensor or the object approaching the electrostatic capacitance sensor is specified based on the pattern of the determination result is water, the control device may stop the determination based on the high-resolution detection mode.

When the water is attached to the electrostatic capacitance sensor (or attached to a cover near the electrostatic capacitance sensor), the following occurs. That is, the electrostatic capacitance of the electrostatic capacitance sensor is changed due to a change in the amount of water or the size of an area in which the water is attached. Therefore, the determination precision at the time of determination of an approach state of an object deteriorates. In the foregoing configuration, the determination based on the high-resolution detection mode is stopped when an object in contact with the electrostatic capacitance sensor or an object approaching the electrostatic capacitance sensor is determined to be water. That is, the electrostatic capacitance detection device does not output a determination result with low precision.

(7) In the electrostatic capacitance detection device, the control device may include a standard capacitor connected to the electrostatic capacitance sensor in series. When the standard capacitor and the electrostatic capacitance sensor are intermittently connected at a first time, the number of connections until a middle potential between the standard capacitor and the electrostatic capacitance sensor reaches a set potential from an initial potential may be detected as a first number of connections. When the standard capacitor and the electrostatic capacitance sensor are intermittently connected at a second time distant from the first time by a predetermined time, the number of connections until the middle potential between the standard capacitor and the electrostatic capacitance sensor reaches the set potential from the initial potential may be detected as a second number of connections. The capacitance change amount may be derived as a number-of-times difference between the first number of connections and the second number of connections.

In this configuration, a change amount of the electrostatic capacitance (that is, a capacitance change amount) of the electrostatic capacitance sensor is detected as a digital value. Therefore, calculation in which the change amount of the electrostatic capacitance of the electrostatic capacitance sensor is used can be simple.

(8) In the electrostatic capacitance detection device, the standard capacitor may be configured to include a plurality of sub-capacitors. The control device may have at least two coupling modes in which the electrostatic capacitance of the standard capacitor is different, as capacitance coupling modes of the plurality of sub-capacitors. In the high-resolution detection mode, the plurality of sub-capacitors may be coupled in a first coupling mode and the capacitance change amount may be detected. In the low-resolution detection mode, the plurality of sub-capacitors may be coupled in a second coupling mode in which the electrostatic capacitance of the standard capacitor is less than in the first coupling mode and the capacitance change amount may be detected. Here, the coupling mode also includes a non-coupling mode (that is, a mode in which one sub-capacitor is not capacitance-coupled with the other sub-capacitor).

In this configuration, the electrostatic capacitance of the standard capacitor is changed according to the coupling mode of the sub-capacitors. Then, the resolution of detection of the change amount of the electrostatic capacitance (that is, the capacitance change amount) of the electrostatic capacitance sensor is allowed to be different by changing the electrostatic capacitance of the standard capacitor. In this way, a structure for changing the resolution of the detection is simple.

(9) In the electrostatic capacitance detection device, the set potential when the number of connections until the middle potential reaches the set potential from the initial potential is detected as the first number of connections or the second number of connections may be set to be changeable. The control device may set the set potential as a first set potential and detect the capacitance change amount in the high-resolution detection mode, and may set the set potential as a second set potential higher than the first set potential and detect the capacitance change amount in the low-resolution detection mode.

In this configuration, the resolution of detection of the change amount of the electrostatic capacitance (that is, the capacitance change amount) of the electrostatic capacitance sensor is set to be different by changing the value of the foregoing set potential. In this way, in the foregoing configuration, a structure for changing the resolution of the detection is simple.

(10) In the electrostatic capacitance detection device, a plurality of electrostatic capacitance sensors may be included, and a first electrostatic capacitance sensor which is one of the plurality of electrostatic capacitance sensors and a second electrostatic capacitance sensor which is another electrostatic capacitance sensor of the plurality of electrostatic capacitance sensors may be disposed away from each other. The control device may detect the capacitance change amounts of the first and second electrostatic capacitance sensors, determine whether the object is in the contact state indicating the state in which the object is in contact with the electrostatic capacitance sensor, the approach state indicating the state in which the object is not in contact with the electrostatic capacitance sensor and the state in which the object is approaching the electrostatic capacitance sensor, or the non-detection state indicating the state in which the object does not approach the electrostatic capacitance sensor based on the capacitance change amounts, and detect motions of the object approaching the first electrostatic capacitance sensor and the second electrostatic capacitance sensor based on a pattern of an overall determination result including a determination result of the first electrostatic capacitance sensor and a determination result of the second electrostatic capacitance sensor obtained during the same period. In this configuration, it is possible to detect a gesture of moving a hand in the vicinity of the electrostatic capacitance detection device.

The electrostatic capacitance detection device can detect a plurality of change modes in which phases are different in a change in electrostatic capacitance.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An electrostatic capacitance detection device comprising:
    an electrostatic capacitance sensor; and
    a control device that controls the electrostatic capacitance sensor,
    wherein the control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount wherein the control device has a high-resolution detection mode and a low-resolution detection mode in which resolution of detection of the electrostatic capacitance is different, as the plurality of detection modes,
    wherein the control device includes a standard capacitor connected to the electrostatic capacitance sensor in series,
    wherein when the standard capacitor and the electrostatic capacitance sensor are intermittently connected at a first time, the number of connections until a middle potential between the standard capacitor and the electrostatic capacitance sensor reaches a set potential from an initial potential is detected as a first number of connections,
    wherein when the standard capacitor and the electrostatic capacitance sensor are intermittently connected at a second time distant from the first time by a predetermined time, the number of connections until the middle potential between the standard capacitor and the electrostatic capacitance sensor reaches the set potential from the initial potential is detected as a second number of connections, and
    wherein the capacitance change amount is derived as a number-of-times difference between the first number of connections and the second number of connections.

2. The electrostatic capacitance detection device according to claim 1,
    wherein based on the capacitance change amount detected in the low-resolution detection mode, the control device determines whether an object is in a contact state indicating a state in which the object is in contact with the electrostatic capacitance sensor.

3. The electrostatic capacitance detection device according to claim 1,
    wherein based on the capacitance change amount detected in the high-resolution detection mode, the control device determines whether the object is in an approach state which is a state in which the object is not in contact with the electrostatic capacitance sensor and a state in which the object is approaching the electrostatic capacitance sensor.

4. An electrostatic capacitance detection device comprising:
    an electrostatic capacitance sensor; and
    a control device that controls the electrostatic capacitance sensor,
    wherein the control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount,
    wherein the control device has a high-resolution detection mode and a low-resolution detection mode in which resolution of detection of the electrostatic capacitance is different, as the plurality of detection modes, and
    wherein the control device determines whether the object is in a contact state indicating the state in which the object is in contact with the electrostatic capacitance sensor, an approach state indicating a state in which the object is not in contact with the electrostatic capacitance sensor and a state in which the object is approaching the electrostatic capacitance sensor, or a non-detection state indicating a state in which the object does not approach the electrostatic capacitance sensor in each of a plurality of the capacitance change amounts obtained continuously in the high-resolution detection mode, and determines a kind of object in contact with the electrostatic capacitance sensor based on a pattern of determination results in the plurality of capacitance change amounts.

5. The electrostatic capacitance detection device according to claim 4,
wherein when a determination result when the object in contact with the electrostatic capacitance sensor or the object approaching the electrostatic capacitance sensor is specified based on the pattern of the determination result is water, the control device stops the determination based on the high-resolution detection mode.

6. The electrostatic capacitance detection device according to claim 1,
wherein the standard capacitor is configured to include a plurality of sub-capacitors,
wherein the control device has at least two coupling modes in which the electrostatic capacitance of the standard capacitor is different, as capacitance coupling modes of the plurality of sub-capacitors,
wherein in the high-resolution detection mode, the plurality of sub-capacitors are coupled in a first coupling mode and the capacitance change amount is detected, and
wherein in the low-resolution detection mode, the plurality of sub-capacitors are coupled in a second coupling mode in which the electrostatic capacitance of the standard capacitor is less than in the first coupling mode and the capacitance change amount is detected.

7. The electrostatic capacitance detection device according to claim 1,
wherein the set potential when the number of connections until the middle potential reaches the set potential from the initial potential is detected as the first number of connections or the second number of connections is set to be changeable, and
wherein the control device sets the set potential as a first set potential and detects the capacitance change amount in the high-resolution detection mode, and sets the set potential as a second set potential higher than the first set potential and detects the capacitance change amount in the low-resolution detection mode.

8. An electrostatic capacitance detection device comprising:
an electrostatic capacitance sensor; and
a control device that controls the electrostatic capacitance sensor,
wherein the control device has a plurality of detection modes for detecting a capacitance change amount corresponding to a change amount of electrostatic capacitance of the electrostatic capacitance sensor, detects the capacitance change amount in each of the plurality of detection modes, and determines presence or absence of contact or approach of an object to the electrostatic capacitance sensor based on the capacitance change amount,
wherein a plurality of the electrostatic capacitance sensors are included, and a first electrostatic capacitance sensor which is one of the plurality of the electrostatic capacitance sensors and a second electrostatic capacitance sensor which is another electrostatic capacitance sensor of the plurality of the electrostatic capacitance sensors are disposed away by a set distance from each other, and
wherein the control device detects the capacitance change amounts of the first and second electrostatic capacitance sensors, determines whether the object is in a contact state indicating a state in which the object is in contact with the electrostatic capacitance sensor, an approach state indicating a state in which the object is not in contact with the electrostatic capacitance sensor and a state in which the object is approaching the electrostatic capacitance sensor, or a non-detection state indicating a state in which the object does not approach the electrostatic capacitance sensor based on the capacitance change amounts, and detects motions of the object approaching the first electrostatic capacitance sensor and the second electrostatic capacitance sensor based on a pattern of an overall determination result including a determination result of the first electrostatic capacitance sensor and a determination result of the second electrostatic capacitance sensor obtained during the same period.

* * * * *